(12) United States Patent
Hartwell

(10) Patent No.: US 9,050,399 B2
(45) Date of Patent: *Jun. 9, 2015

(54) WOUND TREATMENT APPARATUS WITH EXUDATE VOLUME REDUCTION BY HEAT

(71) Applicant: Smith & Nephew PLC, London (GB)

(72) Inventor: Edward Hartwell, York (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/019,932

(22) Filed: Sep. 6, 2013

(65) Prior Publication Data

US 2014/0100538 A1   Apr. 10, 2014

Related U.S. Application Data

(63) Continuation of application No. 12/667,232, filed as application No. PCT/GB2008/050510 on Jun. 27, 2008, now Pat. No. 8,551,061.

(30) Foreign Application Priority Data

Jul. 2, 2007  (GB) .................................. 0712763.2

(51) Int. Cl.
  *A61M 1/00* (2006.01)
  *A61M 27/00* (2006.01)
  (Continued)

(52) U.S. Cl.
  CPC ........... *A61M 1/0023* (2013.01); *A61M 1/0049* (2013.01); *A61M 1/0084* (2013.01);
  (Continued)

(58) Field of Classification Search
  CPC ......... A61M 35/00; A61M 1/00; A61M 3/00; A61M 31/00; A61F 13/00; A61F 13/02; A61F 8/44
  USPC ........................... 604/313, 315, 316, 318, 319
  See application file for complete search history.

(56) References Cited

U.S. PATENT DOCUMENTS 2,280,915 A   4/1942   Johnson
3,874,387 A   4/1975   Barbieri
(Continued)

FOREIGN PATENT DOCUMENTS

CA    2 369 022    10/2001
DE    3 935 818     5/1991
(Continued)

OTHER PUBLICATIONS

The American Heritage® Science Dictionary Copyright © 2005.*
(Continued)

*Primary Examiner* — Tatyana Zalukaeva
*Assistant Examiner* — Ilya Treyger
(74) *Attorney, Agent, or Firm* — Knobbe, Martens, Olson & Bear LLP

(57) ABSTRACT

Apparatus (130) for use in wound therapy of mammals is described, the apparatus (130) comprising: a dressing covering the wound, the dressing being substantially sealed to prevent ingress of ambient atmospheric air to the wound; aspiration means (132) operably connected to a space between the dressing and the wound by an aspiration conduit (142) sealed to the point of entry between wound and dressing against ingress of ambient atmosphere, said conduit (142) being for aspiration of said wound and for removal of fluid from said space between said wound and said dressing; a waste container (148) for receiving aspirated fluid to be discarded operably connected to said aspiration conduit; and heating means (144) for heating said fluid in order to increase the vapor pressure thereof and to cause evaporation to reduce the volume of the fluid in the waste container (148). In a preferred embodiment of the present invention the waste fluid is also provided with a sparge gas.

25 Claims, 6 Drawing Sheets

(51) Int. Cl.
  *A61M 35/00*   (2006.01)
  *A61F 13/00*   (2006.01)
  *A61F 13/02*   (2006.01)
  *A61M 3/00*    (2006.01)
  *A61M 31/00*   (2006.01)
  *A61M 11/00*   (2006.01)

(52) U.S. Cl.
  CPC ............. *A61M1/0088* (2013.01); *A61M 11/00* (2013.01); *A61M 27/00* (2013.01); *A61M 2205/21* (2013.01); *A61M 2205/3379* (2013.01); *A61M 2205/42* (2013.01); *A61M 2205/75* (2013.01); *A61M 1/0027* (2014.02); *A61M 1/0029* (2014.02); *A61M 1/0052* (2014.02); *A61M 1/0098* (2014.02)

(56) References Cited

U.S. PATENT DOCUMENTS

| | | |
|---|---|---|
| 3,993,080 A | 11/1976 | Loseff |
| 4,112,947 A | 9/1978 | Nehring |
| 4,136,696 A | 1/1979 | Nehring |
| 4,184,510 A | 1/1980 | Murry et al. |
| 4,224,945 A | 9/1980 | Cohen |
| 4,316,466 A | 2/1982 | Babb |
| 4,382,441 A | 5/1983 | Svedman |
| 4,465,485 A | 8/1984 | Kashmer et al. |
| 4,540,412 A | 9/1985 | Van Overloop |
| 4,573,965 A | 3/1986 | Russo |
| 4,710,165 A | 12/1987 | McNeil et al. |
| 4,740,202 A | 4/1988 | Stacey |
| 4,778,446 A | 10/1988 | Jensen |
| 4,792,328 A | 12/1988 | Beck et al. |
| 4,795,448 A | 1/1989 | Stacey et al. |
| 4,921,488 A | 5/1990 | Maitz et al. |
| 4,936,834 A | 6/1990 | Beck et al. |
| 4,969,880 A | 11/1990 | Zamierowski |
| 4,979,944 A | 12/1990 | Luzsicza |
| 5,002,539 A | 3/1991 | Coble |
| 5,009,635 A | 4/1991 | Scarberry |
| 5,055,198 A | 10/1991 | Shettigar |
| 5,073,172 A | 12/1991 | Fell |
| 5,100,396 A | 3/1992 | Zamierowski |
| 5,176,663 A | 1/1993 | Svedman et al. |
| 5,261,893 A | 11/1993 | Zamierowski |
| 5,328,614 A | 7/1994 | Matsumura |
| 5,358,494 A | 10/1994 | Svedman |
| 5,380,280 A | 1/1995 | Peterson |
| 5,429,601 A | 7/1995 | Conley et al. |
| 5,449,347 A | 9/1995 | Preen et al. |
| 5,466,229 A | 11/1995 | Elson |
| 5,498,338 A | 3/1996 | Kruger et al. |
| 5,549,584 A | 8/1996 | Gross |
| 5,549,585 A | 8/1996 | Maher et al. |
| 5,636,643 A | 6/1997 | Argenta et al. |
| 5,637,093 A | 6/1997 | Hyman et al. |
| 5,645,081 A | 7/1997 | Argenta et al. |
| 5,759,570 A | 6/1998 | Arnold |
| 5,954,680 A | 9/1999 | Augustine |
| 5,997,733 A | 12/1999 | Wilbur et al. |
| 6,110,197 A | 8/2000 | Augustine et al. |
| 6,135,116 A | 10/2000 | Vogel et al. |
| 6,159,160 A | 12/2000 | Hsei et al. |
| 6,229,286 B1 | 5/2001 | Tokuyama |
| 6,368,311 B1 | 4/2002 | Valerio |
| 6,398,767 B1 | 6/2002 | Fleischmann |
| 6,458,109 B1 | 10/2002 | Henley et al. |
| 6,465,708 B1 | 10/2002 | Augustine |
| 6,520,982 B1 | 2/2003 | Boynton et al. |
| 6,626,827 B1 | 9/2003 | Felix et al. |
| 6,648,862 B2 | 11/2003 | Watson |
| 6,676,610 B2 | 1/2004 | Morton et al. |
| 6,685,681 B2 | 2/2004 | Lockwood et al. |
| 6,695,823 B1 | 2/2004 | Lina et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,764,462 B2 | 7/2004 | Risk, Jr. et al. |
| 6,800,074 B2 | 10/2004 | Henley et al. |
| 6,824,533 B2 | 11/2004 | Risk, Jr. et al. |
| 6,951,553 B2 | 10/2005 | Bubb et al. |
| 7,022,113 B2 | 4/2006 | Lockwood et al. |
| 7,042,180 B2 | 5/2006 | Terry et al. |
| 7,066,949 B2 | 6/2006 | Gammons et al. |
| 7,077,832 B2 | 7/2006 | Fleischmann |
| 7,092,797 B2 | 8/2006 | Gaines et al. |
| 7,108,683 B2 | 9/2006 | Zamierowski |
| 7,128,735 B2 | 10/2006 | Weston |
| 7,144,390 B1 | 12/2006 | Hannigan et al. |
| 7,160,273 B2 | 1/2007 | Greter et al. |
| 7,195,624 B2 | 3/2007 | Lockwood |
| 7,216,651 B2 | 5/2007 | Argenta et al. |
| 7,361,184 B2 | 4/2008 | Joshi |
| 7,367,342 B2 | 5/2008 | Butler |
| 7,494,482 B2 | 2/2009 | Orgill et al. |
| 7,524,315 B2 | 4/2009 | Blott et al. |
| 7,534,927 B2 | 5/2009 | Lockwood |
| 7,540,848 B2 | 6/2009 | Hannigan et al. |
| 7,611,500 B1 | 11/2009 | Lina et al. |
| 7,625,362 B2 | 12/2009 | Boehringer et al. |
| 7,699,830 B2 | 4/2010 | Martin |
| 7,708,724 B2 | 5/2010 | Weston |
| 7,753,894 B2 | 7/2010 | Blott et al. |
| 7,776,028 B2 | 8/2010 | Miller et al. |
| 7,790,945 B1 | 9/2010 | Watson, Jr. |
| 7,794,450 B2 | 9/2010 | Blott et al. |
| 7,811,269 B2 | 10/2010 | Boynton et al. |
| 7,846,141 B2 | 12/2010 | Weston |
| 7,883,494 B2 | 2/2011 | Martin |
| 7,901,672 B2 | 3/2011 | Fraser et al. |
| 7,909,805 B2 | 3/2011 | Weston |
| 7,927,319 B2 | 4/2011 | Lawhorn |
| 7,964,766 B2 | 6/2011 | Blott et al. |
| 7,998,125 B2 | 8/2011 | Weston |
| 8,062,272 B2 | 11/2011 | Weston |
| 8,062,273 B2 | 11/2011 | Weston |
| 8,080,702 B2 | 12/2011 | Blott et al. |
| 8,100,887 B2 | 1/2012 | Weston et al. |
| 8,105,295 B2 | 1/2012 | Blott et al. |
| 8,118,794 B2 | 2/2012 | Weston et al. |
| 8,128,615 B2 | 3/2012 | Blott et al. |
| 8,162,909 B2 | 4/2012 | Blott et al. |
| 8,235,955 B2 | 8/2012 | Blott et al. |
| 8,257,327 B2 | 9/2012 | Blott et al. |
| 8,308,714 B2 | 11/2012 | Weston et al. |
| 8,338,402 B2 | 12/2012 | Fry et al. |
| 8,348,910 B2 | 1/2013 | Blott et al. |
| 8,366,692 B2 | 2/2013 | Weston |
| 8,398,614 B2 | 3/2013 | Blott et al. |
| 8,414,519 B2 | 4/2013 | Hudspeth et al. |
| 8,529,548 B2 | 9/2013 | Blott et al. |
| 8,535,296 B2 | 9/2013 | Blott et al. |
| 8,545,464 B2 | 10/2013 | Weston |
| 8,569,566 B2 | 10/2013 | Blott et al. |
| 2001/0034499 A1 | 10/2001 | Sessions et al. |
| 2002/0050535 A1 | 5/2002 | Igashira et al. |
| 2002/0161346 A1 | 10/2002 | Lockwood et al. |
| 2002/0183702 A1 | 12/2002 | Henley et al. |
| 2002/0198503 A1 | 12/2002 | Risk, Jr. et al. |
| 2002/0198504 A1 | 12/2002 | Risk et al. |
| 2003/0021775 A1 | 1/2003 | Freeman |
| 2003/0040687 A1 | 2/2003 | Boynton et al. |
| 2003/0050594 A1 | 3/2003 | Zamierowski |
| 2003/0097100 A1 | 5/2003 | Watson |
| 2003/0144619 A1 | 7/2003 | Augustine |
| 2003/0171675 A1 | 9/2003 | Rosenberg |
| 2004/0054338 A1 | 3/2004 | Bybordi et al. |
| 2004/0193218 A1 | 9/2004 | Butler |
| 2007/0014837 A1 | 1/2007 | Johnson et al. |
| 2007/0016152 A1 | 1/2007 | Karpowicz et al. |
| 2007/0038172 A1 | 2/2007 | Zamierowski |
| 2007/0055209 A1 | 3/2007 | Patel et al. |
| 2007/0073200 A1 | 3/2007 | Hannigan et al. |

(56) References Cited

U.S. PATENT DOCUMENTS

| | | |
|---|---|---|
| 2007/0118096 A1 | 5/2007 | Smith et al. |
| 2007/0239139 A1 | 10/2007 | Weston |
| 2008/0071216 A1 | 3/2008 | Locke et al. |
| 2008/0071234 A1 | 3/2008 | Kelch et al. |
| 2008/0082059 A1 | 4/2008 | Fink et al. |
| 2008/0200857 A1 | 8/2008 | Lawhorn |
| 2008/0200906 A1 | 8/2008 | Sanders et al. |
| 2008/0234641 A1 | 9/2008 | Locke et al. |
| 2009/0054855 A1 | 2/2009 | Blott et al. |
| 2009/0105671 A1 | 4/2009 | Daggar et al. |
| 2009/0163882 A1 | 6/2009 | Koch et al. |
| 2009/0221977 A1 | 9/2009 | Blott et al. |
| 2009/0306580 A1 | 12/2009 | Blott et al. |
| 2009/0312723 A1 | 12/2009 | Blott et al. |
| 2010/0036367 A1 | 2/2010 | Krohn |
| 2010/0312202 A1 | 12/2010 | Henley et al. |
| 2011/0004171 A1 | 1/2011 | Blott et al. |
| 2011/0009835 A1 | 1/2011 | Blott |
| 2011/0054423 A1 | 3/2011 | Blott et al. |
| 2011/0071483 A1 | 3/2011 | Gordon et al. |
| 2011/0172616 A1 | 7/2011 | Hartwell et al. |
| 2011/0213320 A1 | 9/2011 | Blott et al. |
| 2012/0004628 A1 | 1/2012 | Blott et al. |
| 2012/0041399 A1 | 2/2012 | Blott et al. |
| 2012/0130325 A1 | 5/2012 | Blott et al. |
| 2012/0157942 A1 | 6/2012 | Weston |
| 2012/0259297 A1 | 10/2012 | Blott et al. |
| 2013/0096519 A1 | 4/2013 | Blott |

FOREIGN PATENT DOCUMENTS

| | | |
|---|---|---|
| DE | 4 012 232 | 10/1991 |
| DE | 198 44 355 | 4/2000 |
| EP | 0 020 662 | 7/1984 |
| EP | 0 777 504 | 10/1998 |
| EP | 0 853 950 | 10/2002 |
| FR | 1163907 | 10/1958 |
| GB | 114754 | 4/1918 |
| GB | 641061 | 8/1950 |
| GB | 1224009 | 3/1971 |
| GB | 1549756 | 8/1979 |
| GB | 2195255 | 4/1988 |
| GB | 2378392 | 2/2003 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/19313 | 11/1992 |
| WO | WO 92/20299 | 11/1992 |
| WO | WO 97/27883 | 8/1997 |
| WO | WO 00/07653 | 2/2000 |
| WO | WO 00/50143 | 8/2000 |
| WO | WO 02/083046 | 10/2002 |
| WO | WO 02/092783 | 11/2002 |
| WO | WO 03/053346 | 7/2003 |
| WO | WO 03/101508 | 12/2003 |
| WO | WO 2004/037334 | 5/2004 |
| WO | WO 2005/04670 | 1/2005 |
| WO | WO 2005/105179 * | 4/2005 |
| WO | WO 2005/046760 | 5/2005 |
| WO | WO 2005/105179 | 11/2005 |
| WO | WO 2006/052745 | 5/2006 |
| WO | WO 2006/114637 | 11/2006 |
| WO | WO 2007/013064 | 2/2007 |
| WO | WO 2008/010094 | 1/2008 |
| WO | WO 2008/030872 | 3/2008 |
| WO | WO 2008/036360 | 3/2008 |
| WO | WO 2008/039314 | 4/2008 |
| WO | WO 2008/048481 | 4/2008 |
| WO | WO 2009/158131 | 12/2009 |
| WO | WO 2010/083135 | 7/2010 |

OTHER PUBLICATIONS

Aubrey, D.A., et al., Treatment of the Perineal Wound after Proctectomy by Intermittent Irrigation, Arch. Surg., Oct. 1984, 119, 1141-1144.

Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).

Chariker, M.E., et al, "Effective Management of Incisional and Cutaneous Fistulae with Closed Suction Wound Drainage," Contemporary Surgery. Jun. 1989, pp. 59-63, vol. 34 USA.

Dilmaghani et al., "A Method for Closed Irrigation and Suction Therapy in Deep Wound Infections," Journal of Bone and Joint Surgery, 1969, vol. 51-A, No. 2, pp. 323-342.

Hartz, R.S., et al., Healing of the Perineal Wound, Arch. Surg., Apr. 1980, 115, 471-474.

International Search Report mail Oct. 23, 2008 in International Application No. PCT/GB/2008/050510 in 5 pages.

International Preliminary Report on Patentability and Written Opinion issued Jan. 5, 2010 in International Application No. PCT/GB/2008/050510 in 7 pages.

NURSING75, Wound Suction: Better Drainage with Fewer Problems, Nursing, vol. 5, No. 10, Oct. 1975, pp. 52-55.

Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).

Svedman, P., "Irrigation Treatment in Split-Thickness Skin Grafting of Intractable Leg Ulcers," Scand J. Plast. Reconst. Surg., 19:211-213, 1985.

Svedman, P., "Irrigation Treatment of Leg Ulcers," The Lancet, Sep. 1983, 532-34.

Svedman, P., A Dressing Allowing Continuous Treatment of a Biosurface, IRCS Med. Science: Biomed. Tech.; Clinic. Med.; Surg. and Transplantation, 1979, 7, p. 221.

Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.

Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).

Teder and Svedman et al., "Continuous Wound Irrigation in the Pig," Journal of Investigative Surgery, 1990, vol. 3, pp. 399-407.

Tribble, David E. M.D., An Improved Sump Drain-Irrigation Device of Simple Construction, Archives of Surgery New York, pp. 511-13, 1972 vol. 105.

Vijanto, J. and J. Raekallio, Local Hyperalimentation of Open Wounds, Br. J. surg., 1976, 63, 427-430.

Westaby, S., et al., "A Wound Irrigation Device", The Lancet, Sep. 2, 1978, pp. 503-504.

Wooding-Scott, Margaret, et al., "No Wound is Too Big for Resourceful Nurses," RN Dec. 1988, pp. 22-25 USA.

Zivadinovic, Gorica, Veljko Dukic, Zivan Maksimovic, Dorde Radak and Predrag Pesko, Vacuum Therapy in the Treatment of Peripheral Blood Vessels, Timocki Medicinski Glasnik (Conference Papers of the 5th Timok Medical Days, Majdanepek, 1986), Year XI, Zajecar, 1986, No. 3-4, pp. 161-164 (with English translation).

Japanese Office Action (Notice of Reasons for Rejection), re JP Application No. 2014-022317, dated Dec. 15, 2014.

* cited by examiner

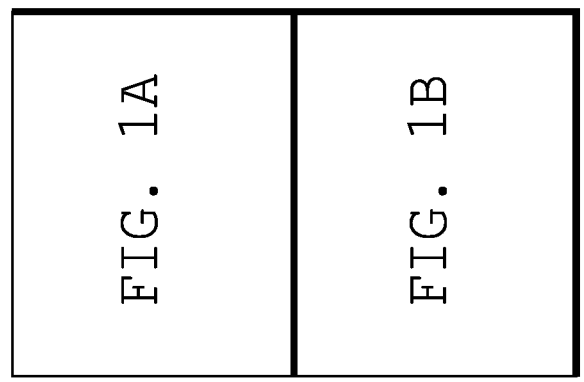

WOUND TREATMENT APPARATUS WITH EXUDATE VOLUME REDUCTION BY HEAT

CROSS-REFERENCE TO RELATED APPLICATIONS

This application is a continuation application of U.S. application Ser. No. 12/667,232, filed Dec. 29, 2009, which is a U.S. National Phase of the International Application No. PCT/GB2008/050510 filed Jun. 27, 2008 designating the U.S. and published on Jan. 8, 2009 as WO 2009/004370, which claims priority of Great Britain Patent Application No. 0712763.2 filed Jul. 2, 2007. The disclosures of these prior applications are incorporated by reference in their entirety.

BACKGROUND

Field of the Disclosure

The present invention relates to apparatus for aspirating, irrigating and/or cleansing wounds, and a method of treating wounds and the exudates from such wounds using such apparatus for aspirating, irrigating and/or cleansing wounds.

The invention relates in particular to such an apparatus and method that can be easily applied to a wide variety of wounds, to cleanse them of materials that are deleterious to wound healing, whilst retaining materials that are beneficial in some therapeutic aspect, in particular to wound healing.

Before the present invention, aspirating and/or irrigating apparatus therefor were known, and tended to be used to remove wound exudate during wound therapy. In known forms of such wound therapy, the offtake from the wound, especially when in a highly exuding state, is voided to waste, e.g. to a collection bag or vessel which is removed when full and discarded as clinical waste. Materials deleterious to wound healing are removed in this way.

The volume of such exudates in some cases is very high and the collection bag or vessel can become relatively rapidly filled. If a collection bag or vessel of greater volume is used to extend the period between which the vessel needs to be emptied or changed this can have disadvantageous consequences on the portability of such apparatus and its convenience of use making the device or apparatus cumbersome and heavy. Furthermore, changing the collection bag or vessel is costly, time consuming and results in cessation of therapy.

In our co-pending International patent application, WO 2004/037334, apparatus, a wound dressing and a method for aspirating, irrigating and cleansing wounds are described. In very general terms, this invention describes the treatment of a wound by the application of topical negative pressure (TNP) therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In our co-pending International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

Our co-pending International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

There are available various forms of apparatus for topical negative pressure (TNP) therapy of wounds, the apparatus being intended to be portable and for use by a patient outside of hospitalisation, for example, in the home, outdoors or even at work so that the therapy can be continuously applied to a wound which does not necessarily require hospitalisation. In such apparatus, a vessel or canister is provided for receiving wound exudates, the canister being gradually filled by aspiration means such as a pump which applies a negative (below atmospheric) pressure. Eventually the canister becomes full and must be removed and discarded and a fresh, empty canister installed. Clearly, the less frequently this canister change is required the better.

In all of the above examples it is clearly beneficial to be able to reduce the volume of exudate which is collected in an apparatus waste container and consequently reduce the weight thereof and also to decrease the frequency at which the waste container need be changed and discarded. This may perhaps be especially so where there is additional fluid being provided to the wound site/dressing for various reasons and which fluid inevitably adds to the volume of waste which is collected and eventually discarded.

It is an object of the present invention to provide apparatus and a method for reducing the rate of collection of waste which eventually needs to be discarded. Consequently, a further objective is to reduce the frequency at which waste containers need to be changed in a given apparatus.

According to a first aspect of the present invention there is provided apparatus for use in wound therapy of mammals, the apparatus comprising:

A dressing covering the wound, the dressing being substantially sealed to prevent ingress of ambient atmospheric air to the wound;

Aspiration means operably connected to a space between the dressing and the wound by an aspiration conduit sealed to the point of entry between wound and dressing against ingress of ambient atmosphere, said conduit being for aspiration of said wound and for removal of fluid from said space between said wound and said dressing;

A waste container for receiving aspirated fluid to be discarded operably connected to said aspiration conduit; and Heating means for heating said fluid in order to increase the vapour pressure thereof and to cause evaporation to reduce the volume of the fluid in the waste container.

In the present invention the dressing is effectively sealed to the skin surrounding the wound. However, the term "sealed" is not an absolute requirement or practically attainable since many flexible dressing membrane materials forming the wound cover are composed of semi-permeable plastics materials which are well known to those skilled in the art. Furthermore, there is almost inevitably some leakage between the skin to which the sealing dressing material is adhered, usually by well known pressure sensitive adhesives, due to hairs and/or other skin surface irregularities and/or imperfections which are not easily completely sealed in absolute terms. The types of self adhesive, flexible dressing drape materials which are ordinarily used in TNP type therapy for sealing membranes over and around wounds are well know to those skilled in the art and will not be elaborated on further herein unless necessary.

In one embodiment of the apparatus according to the present invention, the aspiration means comprises a pump which applies a negative pressure to the wound site in the space between the wound and the sealed dressing. For the avoidance of doubt, the term "negative pressure" used herein means a pressure lower than ambient atmospheric pressure. Such negative pressure is generally at a lowest pressure of 250 mmHg below atmospheric pressure but more usually within a range of 50-200 mmHg below atmospheric pressure.

There are many types of pump which may be used to apply a negative pressure and include peristaltic, vane, diaphragm and the like, for example.

In a TNP apparatus where only a suction force is applied to the wound, the waste material container may be interposed between the aspiration means and the conduit in operable connection to the wound site thus, the aspiration means or pump is applying its negative pressure through the waste container. However, in alternative embodiments the aspiration means may be interposed between the wound site/dressing and the waste container.

The heating means may be any which is suitable for the apparatus in question and may comprise a heating mat or blanket type of material in direct contact with the waste container, for example, or may be associated with the aspiration conduit to heat the waste fluid before it reaches the waste container. Other forms of heating such as cartridge heaters and infrared may be employed. Infrared has the advantage that it is non-contact and the majority of the energy may be coupled into the fluid as suitable non-absorbing canister materials may be chosen.

In alternative embodiments, the heating means may be formed integrally with the waste container or canister and may also include integral thermocouples or thermistors to allow the temperature to be controlled by feedback loop from the control system.

In accordance with the first aspect of the invention an apparatus which is intended for TNP therapy only may be provided in a waste fluid container therefor with one or more filters elements, for example, a hydrophobic filter, which prevents passage or egress of liquid and bacteria but permits egress of vapour, for example, water vapour, in a gaseous state.

Such filter elements, for example, a 0.2 micron pore size filter and/or a 1 micron pore size, may advantageously be incorporated into an exit duct of the waste canister or container. This had the advantage that it provides certainty that the filter has been changed regularly, i.e. when the container has been discarded when full and furthermore, seals the exit duct/container when removed from the apparatus.

In a preferred embodiment of the apparatus of the present invention there is further provided a supply of gas such as air, for example, to the fluid in the waste container which gas supply is in effect a sparge gas supply which may be arranged to pass through the fluid waste to influence constituents such as water, for example, having a lower vapour pressure to be removed preferential by the gas supply. However, the sparge gas may merely discharge into the waste container with the aspirated waste fluid without actually flowing through the waste fluid already collected in the waste container depending upon the arrangement and type of heating means employed.

The waste container also preferably has a connection to pump means to remove the fluid vapour so produced. The pump means may be the same as the aspiration means or may be additional thereto so as to provide a separate flow of gas bubbles through the waste fluid in the waste container. Alternatively or in addition thereto, the gas supply may be a gas bleed provided by suitable valve means to admit a bleed of gas into the aspiration conduit leading from the wound site dressing.

In a further preferred modified embodiment of the present invention the apparatus may further comprise a supply of a gas to the wound site/dressing. Such a gas supply to wound site dressing may be provided by a separate conduit leading into the dressing and may be either a separately provided gas supply or may be a gas bleed into the dressing provided as a bleed gas via suitable valve means and drawn through the dressing by the aspiration means.

The gas may be air or any other suitable gas which is compatible with the wound. This gas supply may, in effect, be the gas supply referred to above as a sparge gas but where the flow of gas is first directed through the wound site/dressing by means of a separate, second bleed gas conduit which is sealed into the wound site/dressing in a similar manner as the aspirant conduit, before being drawn off by the aspiration means to the waste container. The aspirant conduit again allowing the bleed gas supply to be drawn through the waste fluid by the aspiration means. The provision of the bleed gas to the wound site/dressing increase the concentration of volatiles by increasing the surface area and number of nucleation sites for evaporation due to the bubbles and also increases the mass transfer of fluid through the system due to the greater mass of gas passing through the system which in turn is more saturated therefore promoting a greater mass leaving the system.

The provision of a bleed gas may have physiological effects or may serve to reduce the bioburden and/or odour throughout the fluid system of the wound and apparatus by diluting or reacting with or simply flushing through the system more quickly gases such as ozone, nitrous oxide and other gases which may be generated. A gas bleed to the wound site/dressing is particularly beneficial where the wound site/dressing is provided with additional fluid for cleansing and/or irrigation of the wound. The ability to aerate larger quantities of exudates and other fluid prior to reaching the waste container accelerates the evaporation process and removal of liquid which would otherwise accumulate in the waste bottle. It should be understood that the additional fluid supplied to the wound for cleansing and/or irrigation may contain physiologically active agents, may be heated to body temperature, for example, and the exudates from the wound site may be prior treated to remove beneficial agents in the exudates which may be recirculated to the wound, as disclosed in the three co-pending International patent applications of common ownership herewith and mentioned hereinabove, and that only the fluid ultimately destined for the waste container is treated according to the present invention.

In an alternative preferred embodiment the waste fluid may be discharged into the waste container in the form of atomised droplets so as to increase the evaporation rate of the fluid and some of which vapour may be drawn off to a separate receptacle, for example, and discarded.

In a further alternative preferred embodiment the waste fluid may be discharged over the area of a heated plate member in the waste container, for example, the heated plate member being inclined so that the fluid flows relatively slowly to a lower part of the plate member thus having a relatively extended period in which to be heated and being in the form of a relatively thin film. Thus, the rate of evaporation may be increased.

According to a second aspect of the present invention there is provided a method of treating wound exudates with the apparatus according to the first aspect of the present invention.

BRIEF DESCRIPTION OF THE DRAWINGS

In order that the present invention may be more fully understood examples, by way of illustration only, will be described with reference to the following drawings, of which:

FIG. 1 shows a schematic illustration of an apparatus according to a first preferred embodiment of the present invention;

DETAILED DESCRIPTION OF THE PREFERRED EMBODIMENTS

Figure 1A:
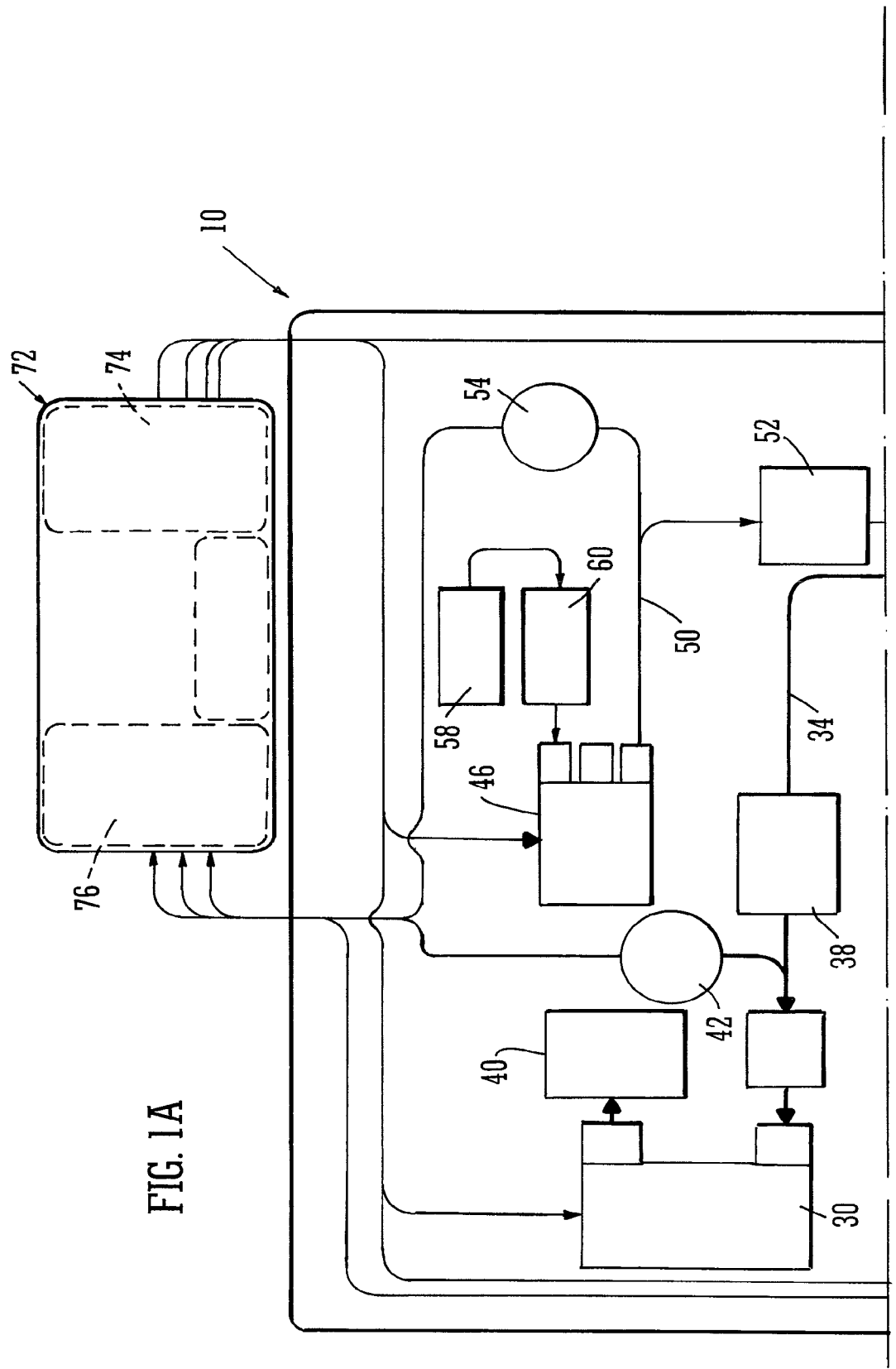
FIG. 1A illustrates a partial view of the apparatus of FIG. 1.
Figure 1B:
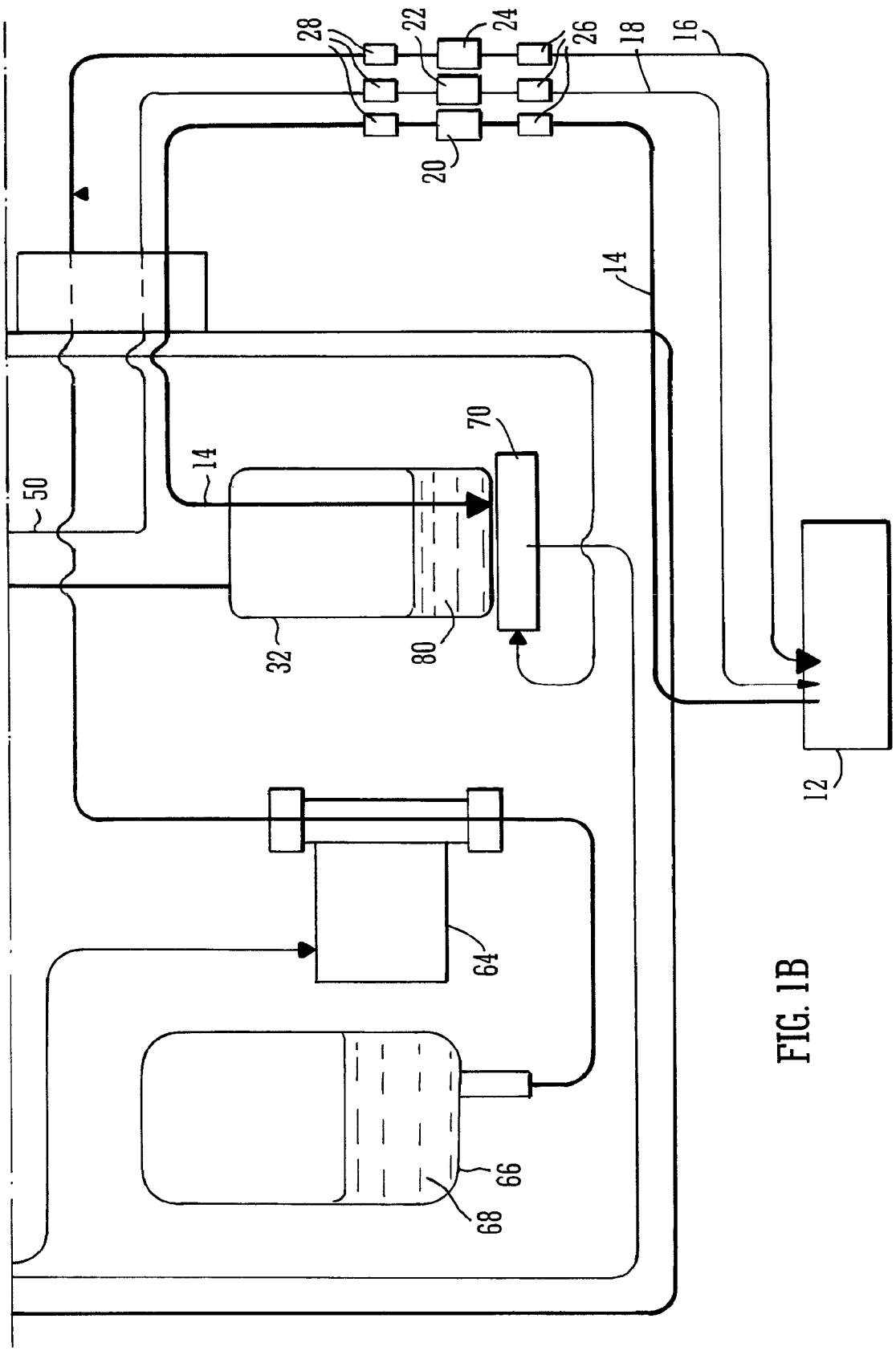
FIG. 1B illustrates a partial view of the apparatus of FIG. 1.

Referring now to the drawings and where FIG. 1A and FIG. 1B show a schematic layout of an apparatus 10 according to the present invention. The schematic shows a "model wound" at 12 made from clear acetate comprising a wound simulating cavity (not shown) into which an aspirant tube 14, an irrigant tube 16 and an air bleed tube 18 are sealed so as to simulate a wound having a sealing dressing. The rectangles 20, 22, 24 denote connectors connecting the three tubes 14, 16, 18 to the appropriate parts of the rest of the apparatus, respectively. Clamps, denoted collectively at 26 and 28 serve to isolate the wound 12 when disconnected from the apparatus or to change one of the tubes or to replace the source of supply relevant to the particular tube. The aspirant tube 14 is connected to a vacuum pump unit 30 via a waste bottle 32 and outlet tube 34 for the application of TNP therapy to the wound 12. The vacuum pump unit 30 is provided with various filter modules 38, 40 to catch "solid" material and suppress odours, respectively. A sensor 42 monitors the vacuum applied by the pump 30 and the vacuum in the waste bottle 32. The air bleed tube 18 is ultimately connected to a vacuum regulator 46 through an extension 50 of line 18 via a filter 52. A wound pressure sensor 54 is also connected to the tube 50 so as to monitor the actual depression at the wound 12. A flow meter 58 and restrictor 60 are provided in the bleed path before the vacuum regulator unit 46. The irrigant tube 16 is connected to a peristaltic pump cassette 64 which in turn is connected to a container 66 of irrigant fluid 68 for the supply of the irrigant fluid 68 to the wound 12. The waste bottle 32 is provided with a heater 70 upon which it sits so as to heat the contents thereof. The whole apparatus is controlled by a control unit 72 which operates on principles well known to those skilled in the electronic control art.

The effect of the vacuum pump 30 aspirating the wound 12 by the tube 14 is to create a vacuum therein so as to draw a supply of bleed air into the wound via the tube 16. The amount of or rate of bleed air is controlled by outputs 74 from the control unit 72 to the vacuum regulator 46 in response to the inputs 76 from the various sensors in the apparatus. Thus, the bleed air is drawn into the wound site by the vacuum applied by the pump 30 and is also withdrawn by the aspiration tube 14 by the vacuum pump together with the wound exudates and the irrigant fluid 68. The waste fluid 80 being withdrawn from the wound site 12 is aerated by the bleed air supply and is delivered to the waste bottle 32 by the tube 14. The waste fluid in the bottle 32 is heated by the heater 70 to a predetermined temperature set in the control system and with the flow of bleed air through the waste fluid 80 vapour is drawn off through the line 34 and discharged via the filter 40.

A system was set up as in the above schematic and the pressure was set up 100 mmHg below atmospheric at the wound site 12. The air bleed was adjusted to 0.2 l/min and the heater 70 set to 65.degree. C. and allowed to stabilise. Saline was used as the irrigant fluid 68 and delivered to the wound 12 at a fixed rate to represent fluid coming from the wound 12. The mass of fluid delivered was recorded together with the mass of fluid collected in the waste bottle 32. For the waste bottle a glass bottle was used with Hawco (trade mark) 20 watt silicon heater mat glued to the base of the bottle. The conditions were by no means optimised but, however, the results indicated that over a 24 hour period a mass of 45 g of fluid was evaporated. Thus, with suitable optimisation of the system it is expected that far higher levels of evaporation may be easily achieved.

Figure 2:
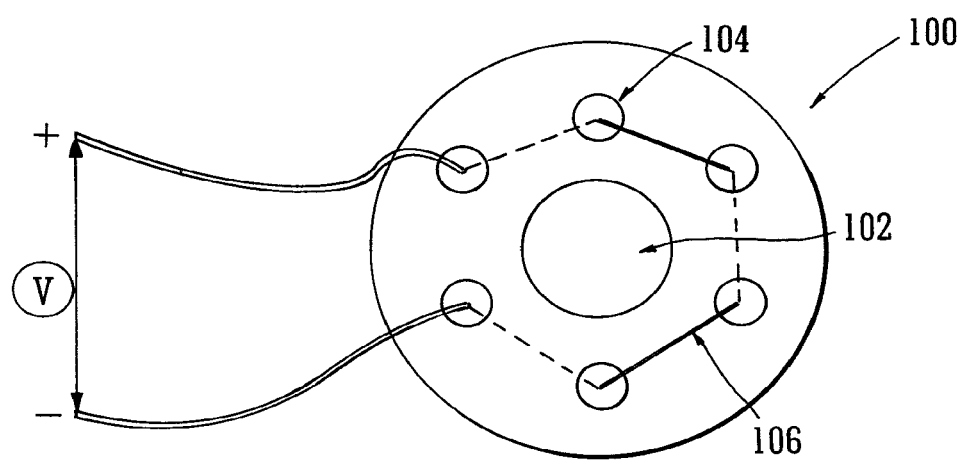
FIG. 2 shows an end view of a heated tube which may be used as the heating means in apparatus according to the present invention.

FIG. 2 shows a heated plastics material tube 100 having seven separate lumens comprising one central lumen 102 for the passage of fluid and six surrounding smaller lumens 104 which were provided with a continuous element of nickel-chrome resistance heating wire 106 which was run up and down the lumens 104 in a continuous manner. The ends of the wire 106 have a voltage applied thereto.

This heating tube may be used in the apparatus of FIG. 1 as, for example, part of the tube 14 immediately prior to entry into the waste bottle 32. With this heating means the surface area to volume ratio of the fluid in contact with the central lumen 102 is relatively high and the fluid may be heated rapidly prior to entry into the waste bottle 32. It will be appreciated by those skilled in the art that this heated tube may be used additionally to the heater 70 shown in FIG. 1 to further enhance the rate of evaporation of fluid.

Figure 3:
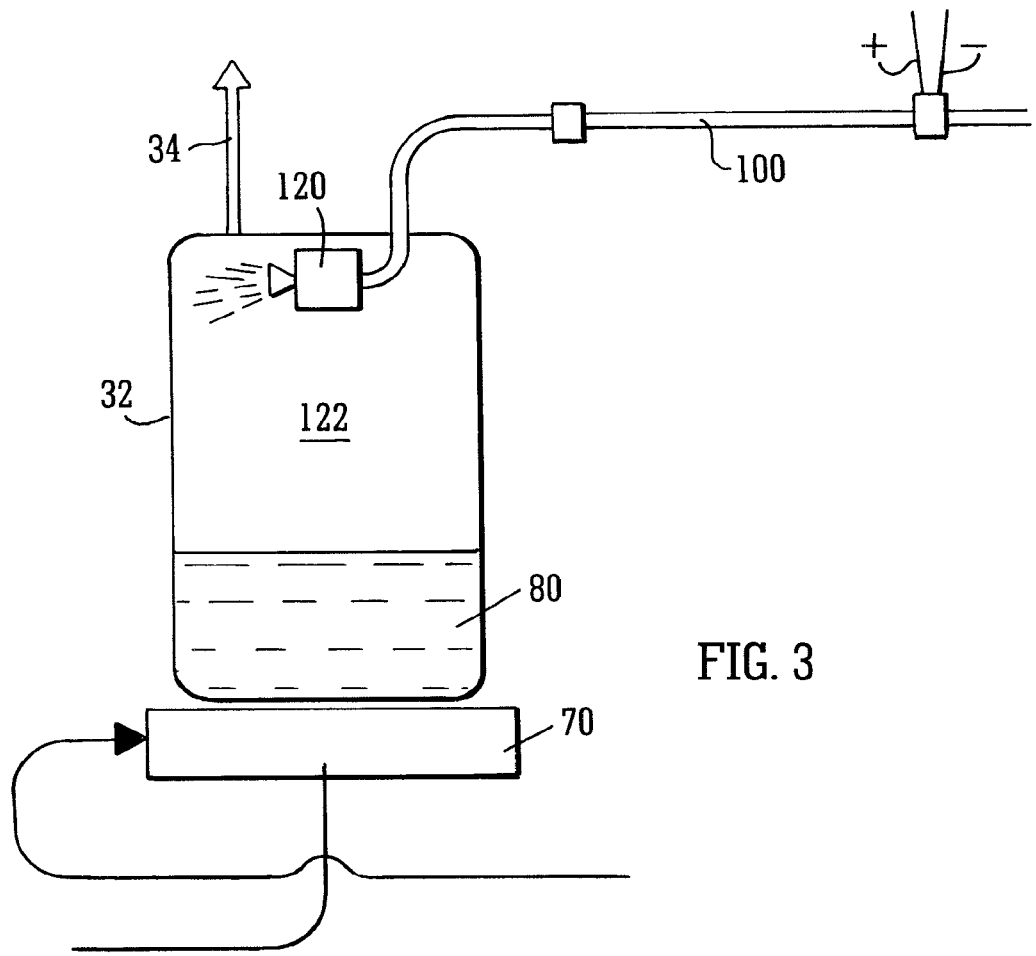
FIG. 3 shows part of a modified apparatus of FIG. 1.

FIG. 3 shows the waste bottle of FIG. 1 modified by the substitution of an atomising spray head 120 in place of the tube 14 which has an end immersed in the waste fluid in bottle 32 in FIG. 1. The spray head 120 terminates above the waste fluid level in the bottle 32 and sprays directly into the free space 122 in the bottle 32. In addition to the spray head 120 this embodiment is further modified by the addition of the heated tube 100 of FIG. 2 so as to preheat the waste fluid prior to entry into the waste bottle 32.

Figure 4:
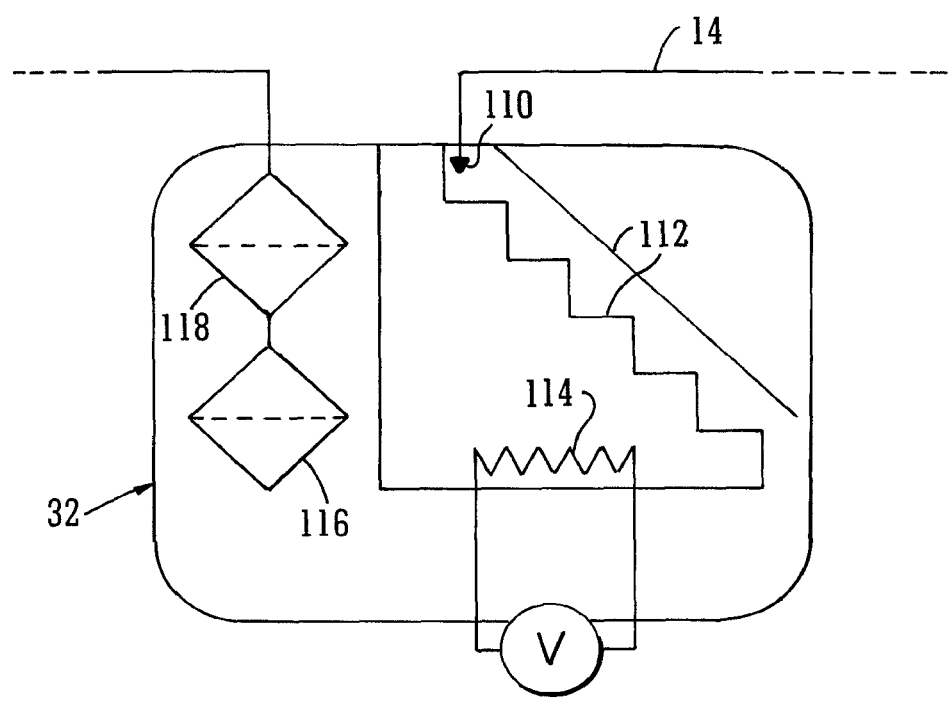
FIG. 4 shows a further modification of part of a modified apparatus of FIG. 1.

FIG. 4 shows a schematic diagram of part of a further modification of the apparatus of FIG. 1. The waste container is indicated by the reference numeral 32 as before as is the inlet aspirant conduit 14. However, in this case the wound exudates and other fluids are discharged by a nozzle 110 over a weir arrangement 112 in the waste container in order to increase the efficiency of heating of the fluid and also to increase the surface area thereof to increase the rate of evaporation. The weir 112 is heated by means of a suitable heating element 114 by a potential difference V controlled by the control unit 72 to maintain a predetermined temperature in response to temperature signals from a sensor (not shown). The waste container 32 is provided with filters 116, 118 which allow the passage of gaseous vapour but not liquid.

Figure 5:
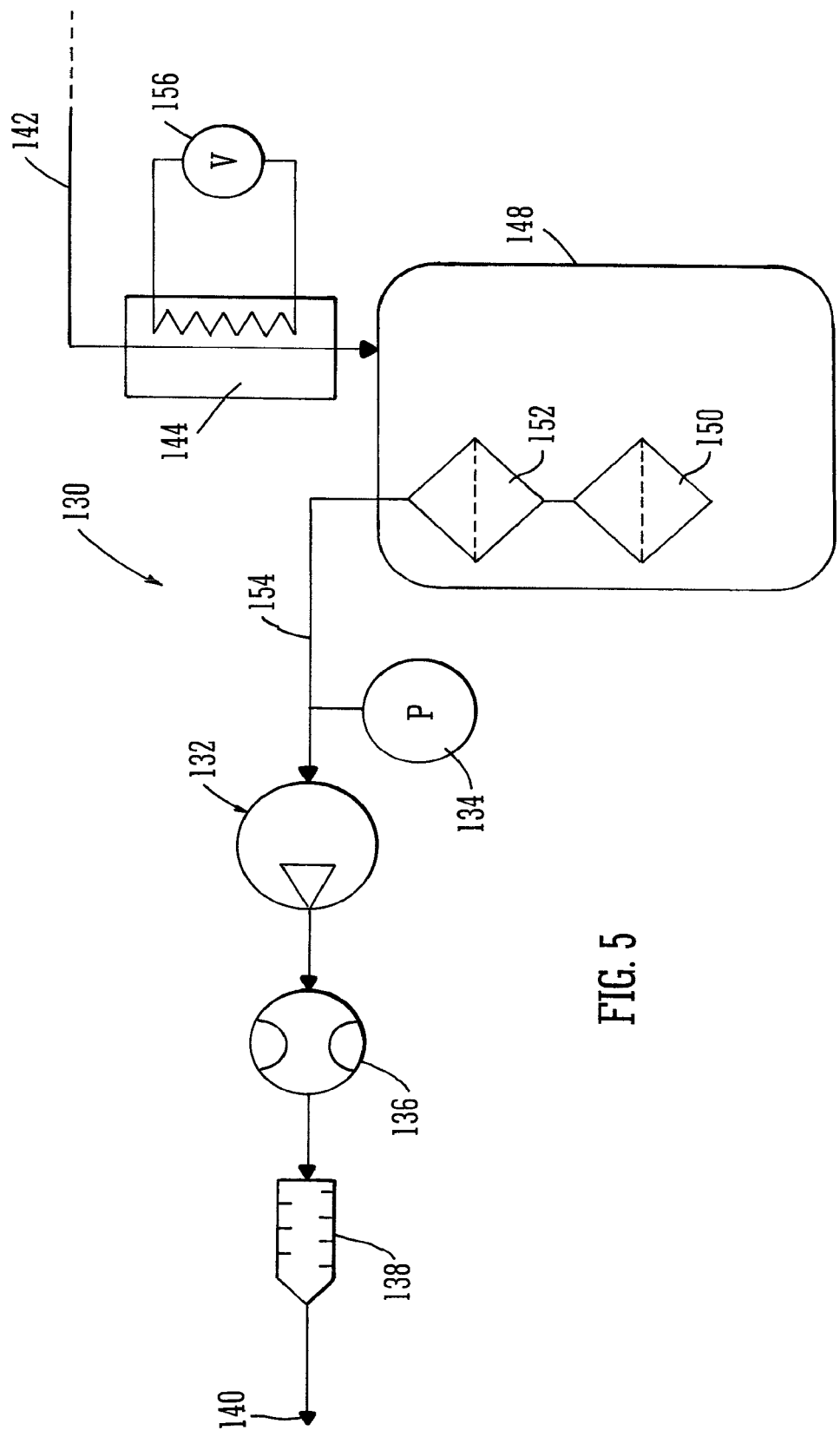
FIG. 5 which shows a schematic arrangement of a portable TNP type apparatus embodying the present invention.

FIG. 5 shows a schematic representation of part of a portable TNP therapy apparatus 130. The apparatus comprises a device including a pump 132, a pressure monitor 134 to monitor pressure applied by the pump at a wound site (not shown), a flow meter 136 and a silencer 138 to quieten gas/vapour being exhausted by the pump through an exhaust orifice 140. The pump aspirates a wound site via an aspiration tube or conduit 142 and draws the aspirated fluid through a heated conduit 144, which may be the same or similar to heated conduit described with reference to FIG. 2, immediately into a waste canister 148 which is equipped with filters 150, 152 which ensure that only gaseous vapour and/or gas is drawn from the canister 148 via an exit conduit 154. The conduit 144 has a voltage 156 applied across a resistance heater the voltage being controlled by a control system (not shown) located in a device housing (not shown) together with the pump, pressure sensor, flow meter etc. A desired temperature may be preset in the control system to be maintained thereby in response to signals from a temperature sensor (not shown) incorporated into the heated conduit in known manner.

What is claimed is:

1. A negative pressure wound therapy apparatus comprising:
    a dressing configured to cover a wound;
    a source of negative pressure configured to be in fluid communication with the dressing, the source of negative pressure further configured to aspirate fluid from the wound;
    a collection canister configured to be in fluid communication with the dressing and the source of negative pressure, the collection canister further configured to receive fluid aspirated from the wound; and
    a volume reduction mechanism positioned downstream of the dressing so as to be applied to fluid removed from the wound, the volume reduction mechanism configured to increase vapor pressure of fluid aspirated from the wound and to cause at least some of the fluid to evaporate so that volume of the fluid aspirated from the wound is reduced.

2. The apparatus according to claim 1 further comprising an aspiration conduit for aspiration of the wound and for removal of fluid from the wound.

3. The apparatus according to claim 2 wherein the collection canister is interposed between the source of negative pressure and the aspiration conduit in operable connection to the wound.

4. The apparatus according to claim 1 wherein the volume reduction mechanism comprises a resistance heated article.

5. The apparatus according to claim 4 wherein the article is a mat or blanket in contact with the collection canister.

6. The apparatus according to claim 4 wherein the article is a conduit through which the fluid aspirated from the wound passes.

7. The apparatus according to claim 4 wherein the article is a heated weir over which the fluid aspirated from the wound flows.

8. The apparatus according to claim 1 wherein a portion of the collection canister is configured so as to permit passage of gaseous vapor but not liquid out of the collection canister.

9. The apparatus according to claim 1 further comprising a gas supply.

10. The apparatus according to claim 9 wherein the volume reduction mechanism comprised the gas supply arranged to pass through the fluid aspirated from the wound in the collection canister.

11. The apparatus according to claim 9 wherein the gas supply is a bleed gas provided by valve means.

12. The apparatus according to claim 9 wherein the gas supply is arranged to first flow through the dressing covering the wound before being aspirated from the wound.

13. The apparatus according to claim 12 wherein the gas supply through the dressing is provided via a separate conduit into the dressing covering the wound.

14. The apparatus according to claim 1 wherein the aspirated fluid is discharge into the collection canister via an atomising nozzle.

15. The apparatus according to claim 1 wherein an aspiration pump is interposed between the collection canister and the aspiration conduit.

16. The apparatus according to claim 9 wherein the gas supply is in communication with at least one of the collection canister, the dressing, and an aspiration conduit.

17. The apparatus according to claim 9, wherein the gas supply is a sparge gas supply.

18. The apparatus according to claim 9, comprising one or more pumps.

19. The apparatus according to claim 9, wherein the collection canister comprises a pump to remove vapor within the collection canister.

20. The apparatus according to claim 1, wherein the volume reduction mechanism comprises at least one of a cartridge heater and an infrared heater.

21. The apparatus according to claim 1, further comprising one or more thermocouples or thermistors.

22. A method for treating a wound comprising:
    positioning a dressing over a wound;
    reducing the pressure beneath the dressing;
    removing wound exudate fluid from the wound;
    evaporating at least some of the fluid removed from the wound with a volume reduction mechanism positioned downstream of the dressing to reduce the volume of such fluid; and
    collecting the remaining fluid.

23. The method for treating a wound according to claim 22, comprising heating the fluid removed from the wound to reduce the volume of the fluid.

24. The method for treating a wound according to claim 22, comprising passing a gas through the fluid removed from the wound to reduce the volume of the fluid.

25. The method for treating a wound according to claim 22, further comprising removing a fluid vapor with a pump.

* * * * *